(12) United States Patent
Snuparek et al.

(10) Patent No.: US 7,619,087 B2
(45) Date of Patent: Nov. 17, 2009

(54) METHOD OF PREPARATION OF OXYCODONE

(75) Inventors: Vladislav Snuparek, Risnovce (SK); Lubica Ratkovska, Hlohovec (SK); Bohumil Proksa, Hlohovec (SK)

(73) Assignee: Zentiva, a.s., Hlohovec (SK)

( * ) Notice: Subject to any disclaimer, the term of this patent is extended or adjusted under 35 U.S.C. 154(b) by 679 days.

(21) Appl. No.: 10/569,423

(22) PCT Filed: Aug. 16, 2005

(86) PCT No.: PCT/SK2005/000014

§ 371 (c)(1),
(2), (4) Date: Feb. 23, 2006

(87) PCT Pub. No.: WO2006/019364

PCT Pub. Date: Feb. 23, 2006

(65) Prior Publication Data

US 2007/0088162 A1    Apr. 19, 2007

(30) Foreign Application Priority Data

Aug. 18, 2004    (SI) .................................. 321-2004

(51) Int. Cl.
*C07D 489/08* (2006.01)
*C07D 489/02* (2006.01)

(52) U.S. Cl. .......................................... 546/45; 546/44
(58) Field of Classification Search ................... 546/45, 546/44
See application file for complete search history.

(56) References Cited

U.S. PATENT DOCUMENTS 7,071,336 B2 * 7/2006 Francis et al. ................. 546/45

OTHER PUBLICATIONS

Krassnig, Roland et al:, " Optimization of the synthesis of oxycodone and 5-methyloxycodone"., Archiv Der Pharmazie, vol. 329, pp. 325-326, 1996.

* cited by examiner

*Primary Examiner*—Charanjit S Aulakh
(74) *Attorney, Agent, or Firm*—Oblon, Spivak, McClelland, Maier & Neustadt, L.L.P.

(57) ABSTRACT

A method of preparation of Oxycodone of formula I by reacting thebaine of formula II, or its analogue of formula III, wherein R represents a $C_2$ to $C_5$ alkyl, an alkylaryl, preferably benzyl, methoxybenzyl, or allyl, with hydrogen peroxide or peroxoacids in the presence of oxalic acid in admixture with acetic or formic acid. From the resulting crystalline precipitate of 14-hydroxycodeinone oxalate, by addition of a base, 14-hydroxycodeinone of formula IV is released, which is hydrogenated with hydrogen in the presence of a catalyst to yield Oxycodone (I): Oxycodone is transformed to hydrochloride, which is used as the active ingredient in analgesic formulations.

15 Claims, No Drawings

METHOD OF PREPARATION OF OXYCODONE

TECHNICAL FIELD

This invention relates to pharmaceutical production, namely to preparation of Oxycodone (1), which is a strong analgesic agent, used in the form of its hydrochloride in therapeutic practice, or is used as an intermediate product during production of morphine antagonists such as Naloxone or Naltrexone.

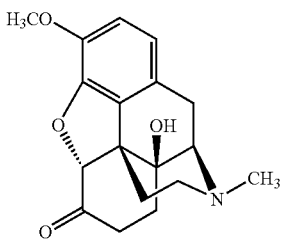

(I)

BACKGROUND ART

Oxycodone (I) is produced by two principal methods:

a) Transformation of thebaine (II), a natural alkaloid isolated from the plant *Papaver somniferum* L., or its analogs (III), wherein R represents an alkoxy- or amino-alkyl residue. During this procedure (Scheme 1), thebaine (II) reacts in an acidic environment with hydrogen peroxide, peroxoacids or other oxidizing agents to form 14β-hydroxycodeinone (IV), which is hydrogenated to provide Oxycodone (I).

Scheme 1

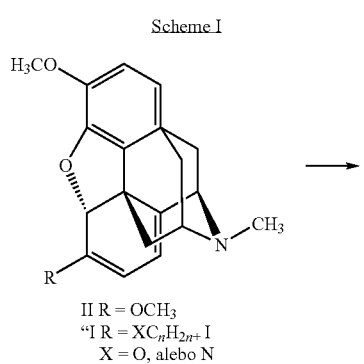

II R = OCH$_3$
"I R = XC$_n$H$_{2n+1}$
X = O, alebo N

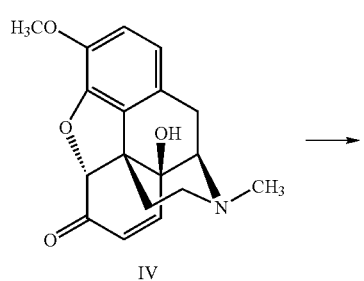

IV

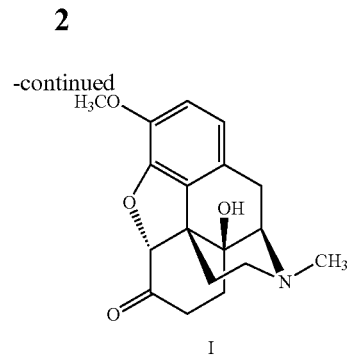

I

Thebaine, dissolved in hot concentrated acetic acid, is transformed to 14β-hydroxycodeinone by reaction with 30% hydrogen peroxide (Freund M., Speyer E.: J. Prakt. Chem. 94, 135 (1916); Lutz R. E., Small L : J. Org. Chem. 4, 220-233 (1939); DE 286431) with a ca. 30% yield. About the same yield was obtained also in oxidation of thebaine (II) with chromic acid (DE 286431; DE 411530) or with manganese acetate (Viebock F.: Chem. Ber. 67, 197 (1934)). A significantly higher yield (about 75%) was recorded when thebaine (II) was reacted with hydrogen peroxide in acetic acid at a temperature not exceeding 40° C. (Feldmann I. Ch., Liutenberg A. I.: Zh. Prikl. Khim. 18, 715 (1945)), or in a mixture of sulfuric acid and 88% formic acid (Krassnig R., Hederer Ch., Schmidhammer H.: Arch.Pharm. 329, 325 (1996)).

Comparable results were achieved when thebaine (II) was reacted with peroxoacids, for example m-chloroperbenzoic acid in a mixture of acetic acid and trifluoroacetic acid (Hauser F. M., Chen T-K., Carroll F. I.: J. Med. Chem. 17, 1117 (1974)); but Iijima et al. concluded that this reaction does not provide reproducible yields (about 25%) and a lot of undesirable products are formed (Iijima I., Rice K. C., Brossi, A.: Helv. Chim. Acta 60, 2135 (1977)).

In a modified procedure, instead of thebaine (II) codeine (V) can be used, Scheme 2, which is first oxidized to codeinone (VI), which, by reaction with either acylating or alkylating agents, provides an enolether/ester VII (EP 889045, U.S. Pat. No. 5,869,669, U.S. Pat. No. 4,639,520), essentially a thebaine analogue, which is further gradually transformed to 14β-hydroxycodeinone (IV) by any of the above-mentioned methods.

Scheme 2

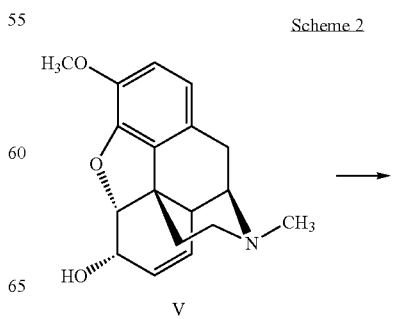

V

-continued

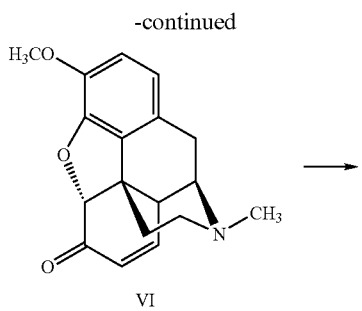

VI

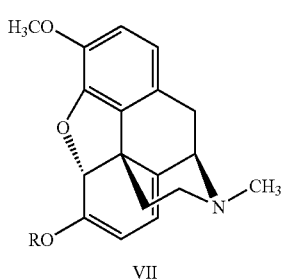

VII

It is also possible to classify the Sankyo process (GB 1,260, 699) in this group, which process issues from codeinone (VI), which provides codeinone pyrrolidinylenamine (VIII) with pyrrolidine in aprotic solvents, Scheme 3. Subsequent reaction with hydrogen peroxide, chromic acid, organic peroxyacids (peracetic, perbenzoic) or permanganate, in the environment of aqueous acetic acid, phosphoric acid, etc., provides 14-hydroxycodeinone (IV).

Scheme 3

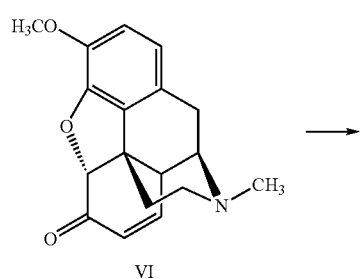

VI

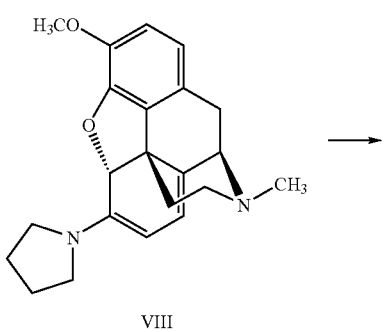

VIII

-continued

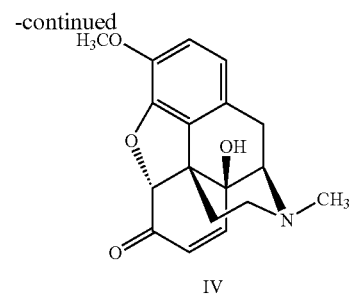

IV b) Oxidation of codeinone (VI) by action of peroxoacids, of combination of organic acids and hydrogen peroxide, or of inorganic oxidizing agents (e.g. $Co^{3+}$ salts), with a maximum yield of 57% of 14β-hydroxycodeinone, which is hydrogenated to Oxycodone (I) (Coop A., Rice K. C.: Tetrahedron 55, 11429 (1999)).

The C-7-C-8 double bond of 14β-hydroxycodeinone was hydrogenated catalytically according to CH 751 10 (U.S. Pat. No. 1,468,805) on Pt black, colloidal Pd, or in the presence of $PdCl_2$ (U.S. Pat. No. 1,485,673) in diluted acetic acid. Ijima used Pd/BaSO4 as the catalyst in this reaction (J. Med. Chem. 21, 398 (1978)), as well as Lutz R. E. and Small L. (J. Org. Chem. 4, 220 (1939)); the use of 10% Pd/C in concentrated acetic acid has also been known (Krassnig R., Hederer Ch., Schmidhammer H.: Arch. Pharm. 329, 325 (1996)) with the yield of about 70%. Feldmann and Liutenberg (Zh. Prikl. Khim. 18, 715 (1945)) hydrogenated the hydrochloride of 14β-hydroxycodeinone on Raney-Ni in hot ethanol with the yield of 74% hydrochloride of Oxycodone.

All the mentioned methods of preparation of Oxycodone (I) have drawbacks that the reaction of peroxide/peroxoacids with thebaine or its analogues does not yield unambiguously reproducible results, a mixture of badly separable byproducts is formed, and the yields are low.

These drawbacks have been rectified by the method of the present invention.

DISCLOSURE OF INVENTION

The present invention provides a method of preparation of Oxycodone of formula I by reaction of thebaine (II) or its analogues of formula III, wherein R represents a $C_2$ to $C_5$ alkyl, an alkylaryl, preferably benzyl, methoxybenzyl, or allyl,

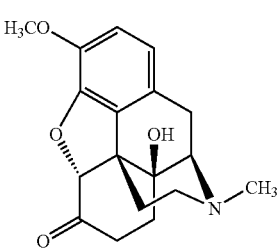

I

-continued

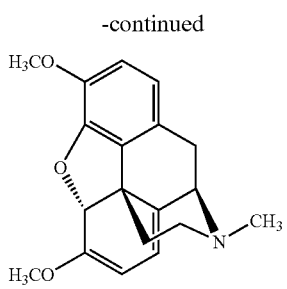

II

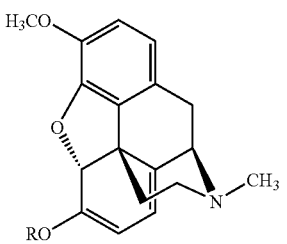

III with hydrogen peroxide or peroxoacids such as peracetic acid, perbenzoic acid or m-chloroperbenzoic acid, in the presence of oxalic acid and of another organic acid, e.g. formic acid or acetic acid, wherein a crystalline precipitate of 14-hydroxycodeinone oxalate is formed, from which precipitate, by addition of a base, 14-hydroxycodeinone of formula IV is released, which is hydrogenated with hydrogen in the presence of a catalyst to yield Oxycodone (I).

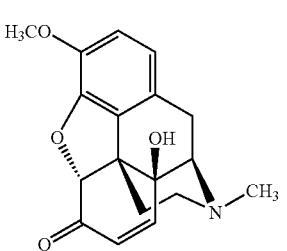

IV

Reaction of thebaine or of its analogues of formula III with hydrogen peroxide or peroxoacids in the presence of oxalic acid and of another organic acid yields 14-hydroxycodeinone, which, with oxalic acid, forms a poorly soluble crystalline precipitate of 14-hydroxycodeinone oxalate. In this way the equilibrium of conversion of thebaine is shifted and subsequent and undesired side reactions are suppressed, such as oxidation of thebaine to trans-10-hydroxythebaine or addition of water to 14-hydroxycodeinone yielding (8S)-hydroxyoxycodone, etc.

When formic acid is used as the other organic acid, its concentration is preferably 80 to 90%, more preferably 88%. The concentration of hydrogen peroxide is preferably 25 to 33%. The molar ratio of thebaine or its analogue:oxalic acid: the other organic acid:hydrogen peroxide or peroxoacid is preferably 0.8-2:1:2.0-3.0:2.0-3.0, more preferably 1.5-2.0: 1:2.3-2.7:2.3-2.7.

The temperature during the reaction of thebaine or its analogues with hydrogen peroxide or peroxoacids is preferably 0 to 35° C., more preferably 15 to 25° C.

In the prior processes, the oxidation of thebaine/thebaine analogs has been carried out with hydrogen peroxide/peroxoacids in the presence of an organic or inorganic acid (what is important is protonization of the nitrogen in the thebaine molecule in order to avoid formation of an N-oxide, or to achieve required solubility of the substrate).

The process of Krassnig R. et al., Arch. Pharm. 329, 325 (1996) uses a mixture of thebaine, sulfuric acid, formic acid and hydrogen peroxide; the system is homogeneous throughout the whole reaction. After completion of oxidation the reaction mixture is poured onto ice and alkalized by addition of ammonium hydroxide. The product, 14-hydroxycodeinone, is extracted with dichloromethane.

The advantage of the process according to the present invention resides in the fact that oxidation of thebaine/its analogs with hydrogen peroxide or peroxoacids in the presence of oxalic acid and another organic acid (formic, acetic) produces a precipitate of the product (14-hydroxycodeinone, resulting in a heterogeneous system, which shifts the equilibrium of the oxidation reaction and avoid subsequent reactions of the product (14-hydroxycodeinone) with the oxidizing agent, thus leading to higher conversion and purer product. After completion of the reaction the reaction mixture (suspension) is cooled down, alkalized (releasing the 14-hydroxycodeinone base from its salts) and the product precipitate (14-hydroxycodeinone) is filtered off, washed and dried. This process offers a higher yield and purer product than the prior processes.

In the known processes (e.g. Arch. Pharm. 329, 325 (1996)) of reaction of thebaine with hydrogen peroxide in the presence of sulfuric acid and formic acid, the yield of 14-hydroxycodeinone was 74.3% and 78.5%, resp., and the product purity was 88.3% and 90.1% (25° C.), resp.

In the method according to this patent, using the molar ratio of reactants thebaine:oxalic acid:formic acid:hydrogen peroxide=16:8.6:22:21, the yield was 91.3% and the product purity was 93.3% (25° C.).

The reaction mixture, which is constituted by a suspension of 14-hydroxycodeinone oxalate in the reaction medium, after the conversion of introduced thebaine, can be processed by separating the suspension by centrifuging, decantation or filtration, dissolving 14-hydroxycodeinone oxalate in hot water, and precipitating, by adjusting pH with addition of a base, 14-hydroxycodeinone, which is separated, washed and dried. Another method of isolation of 14-hydroxycodeinone represents a procedure wherein the reaction mixture in which 14-hydroxycodeinone oxalate is dispersed is alkalized by addition of a base to adjust pH to 9-10, preferably 9.2-9.6, 14-hydroxycodeinone is separated by centrifugation or filtration, or optionally extracted from the alkaline environment with an organic solvent.

14-hydroxycodeinone prepared by this method is hydrogenated by a known method in the presence of a catalyst from the group of rare metals, such as Pt or Pd, or Ni, in an aqueous solution of an organic acid, for example acetic acid. The prepared Oxycodone is precipitated from the reaction medium by adjusting pH with addition of an alkali; the precipitate is separated by filtration or centrifugation and the product is dried.

Oxycodone is dissolved in diluted hydrochloric acid at temperature of 70 to 90° C. and Oxycodone hydrochloride starts to crystallize upon slow cooling down. The procedure yields the product, Oxycodone hydrochloride, in the form of crystals characterized by RTG diffraction analysis, the results of which are presented in Table 1.

Oxycodone or Oxycodone hydrochloride, prepared according to this invention, can be used as the active ingredient in pharmaceutical formulation, containing further at least one pharmaceutically acceptable excipient.

TABLE 1

Characteristic peaks in the RTG diffraction
pattern of Oxycodone hydrochloride

| 2Θ° | RI [%] |
|---|---|
| 8.30 | 85 |
| 10.04 | 37 |
| 10.70 | 79 |
| 11.34 | 39 |
| 12.06 | 96 |
| 12.86 | 34 |
| 13.94 | 56 |
| 14.52 | 34 |
| 16.20 | 100 |
| 17.16 | 44 |
| 17.68 | 78 |
| 18.24 | 73 |
| 19.10 | 79 |
| 20.26 | 82 |
| 21.54 | 41 |
| 23.48 | 44 |
| 23.98 | 53 |
| 25.14 | 58 |
| 26.00 | 35 |
| 27.10 | 34 |
| 27.64 | 29 |
| 28.10 | 44 |
| 28.92 | 33 |
| 29.32 | 26 |
| 29.98 | 44 |
| 31.14 | 21 |
| 33.28 | 29 |
| 33.72 | 26 |
| 34.26 | 25 |
| 35.06 | 36 |
| 35.66 | 21 |
| 36.84 | 18 |
| 38.18 | 20 |
| 38.98 | 18 |
| 40.36 | 18 |
| 42.96 | 18 |
| 44.10 | 27 |
| 44.88 | 19 |
| 45.84 | 16 |
| 47.56 | 17 |

The present method is advantageous in that it allows obtaining a product with low content of impurities in yields highly exceeding the data described in the art.

The following examples describe the method according to this invention in more detail; however, they do not limit its extent in any respect.

EXAMPLES

Example 1 a) 18.66 kg of oxalic acid is dissolved in water, 84.8 kg of thebaine is added, and after it has dissolved, 19.50 kg of 88% formic acid and 42.4 kg of 30% hydrogen peroxide are added. The reaction mixture is stirred at 25° C. until total conversion of thebaine (determined by capillary electrophoresis; capillary 50 cm×0.05 mm, electrolyte 100 mM TRJS/phosphate, pH 2.7, 5 mM dimethoxy-β-cyclodextrin, temperature 25° C. 30 kV; thebaine migration time 5.6 min). The reaction mixture is cooled down to 5° C., 10% aqueous solution of KOH is added with stirring until pH of 9.2. Precipitated crystals of 14-hydroxycodeinone are centrifuged off, washed with water and dried. Ca. 76 kg of 14-hydroxycodeinone (89%) is obtained.

b) 72.50 kg of 14-Hydroxycodeinone is dissolved in 10% aqueous solution of acetic acid, 5% Pd/C catalyst is added, and the mixture is hydrogenated under overpressure of electrolytic hydrogen 104 to 106 kPa at temperatures 30 to 35° C. The reaction mixture is diluted with 200 l of water, filtered, the filtrate is cooled down to 5° C. and Oxycodone base is precipitated by adjusting pH with an addition of an ethanolic solution of ammonia to the value 9.2. The suspension is centrifuged, Oxycodone is washed with water and dried at 70 to 80° C. At least 67 kg (92%, purity 98.5%) of Oxycodone is obtained.

c) An aqueous solution of HCl (87.0 kg of water and 13.00 kg of conc. HCl) is stirred with 48 kg of Oxycodone base at 80° C., activated carbon and diatomaceous earth are added and, after stirring for 15 min, the suspension is filtered, the filtrate is gradually cooled down to the final temperature of 1 to 3° C. Precipitated crystals are centrifuged off, washed with ethanol, and Oxycodone hydrochloride is dried at temperature of about 70 to 80° C. 51.2 kg of (91%) Oxycodone hydrochloride is obtained, m.p. 219° C, $[\alpha]_D^{20}$—145°, water content 6.0%, purity 99.4% (RP C8 column, 150×3.9 mm, 5 µm, with a RP C8 pre-column, 20×3.9 mm, 5 µm, mobile phase 0.005 mol/l sodium hexane sulfonate-methanol-phosphoric acid-triethyl-amine (v/v) (900:100:5:2), pH=2.5 adjusted with NaOH; flow rate 1.5 ml/min; temperature 50° C.; UV, λ=206 run), content 100.03% (titration).

Example 2

Thebaine (1 kg) is dissolved in an aqueous solution of oxalic acid (0.21 kg in 1 l water). 0.23 kg of 88% formic acid and 0.81 kg of peracetic acid (39%) are added. The reaction mixture is stirred at 25° C. resulting in consumption of thebaine (evaluated by CZE). The reaction mixture is cooled down to 5° C., 10% aqueous solution of sodium hydroxide is added with stirring until pH of 9.2. Precipitated crystals of 14-hydroxycodeinone are centrifuged off, washed with water and dried. Ca. 0.92 kg of 14-hydroxycodeinone (91.8%) is obtained. Further procedure of preparation of Oxycodone hydrochloride according to Example Ib) and Ic).

Example 3

6-Benzyloxy-4,5α-epoxy-3-methoxy-17-methylmorfina-6,8(14)-diene (52.5 g) is dissolved in a solution prepared by dissolving 9.8 g of oxalic acid in 35 ml of water, 10 ml of acetic acid and 21.2 ml of 30% hydrogen peroxide are added. The reaction mixture is stirred at 20° C. until total conversion of the benzyl analogue of thebaine, the reaction mixture is cooled down to 2° C., 8% aqueous solution of NaOH is added with stirring until pH of 9.2. Precipitated crystals of 14-hydroxycodeinone are filtered off, washed with water and dried. The procedure yields ca. 37 g of 14-hydroxycodeinone (82%). Further procedure of preparation of Oxycodone hydrochloride is the same as in Example Ib) and Ic).

Example 4

4,5α-Epoxy-6-ethoxy-3-methoxy-17-methylmorfina-6,8(14)-diene (22.1 g) is dissolved in a solution (10 g of oxalic acid in 35 ml of water); formic acid (9.8 ml, 88%) and hydrogen peroxide (21.2 ml) are added. The mixture is stirred at 30° C. for 30 hrs, cooled down to 10° C., precipitated 14-hydroxycodeinone oxalate is filtered off and washed. Wet 14-hydroxycodeinone oxalate is dissolved in 80 ml of water at 65° C. and 10% potassium hydroxide is added until pH of 9.3, the suspension of 14-hydroxycodeinone is cooled down to 15° C., the solids are filtered off, washed and dried. Ca. 17.6 g of 14-hydroxycodeinone (yield 83%, purity 93.2%) is obtained.

INDUSTRIAL APPLICABILITY

Manufacture of Oxycodone of formula I and its hydrochloride described herein offers a significant advantage with respect to economic demand factor and environmental burden compared to the known methods. Oxycodone hydrochloride is used to produce pharmaceuticals with analgesic effects.

The invention claimed is:

1. A method of preparation of Oxycodone of formula I,

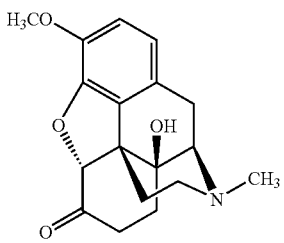

I wherein thebaine of formula II, or its analogue of formula III, where R represents a $C_2$ to $C_5$ alkyl, an alkylaryl, or allyl,

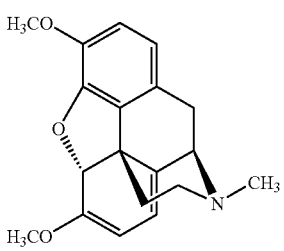

II

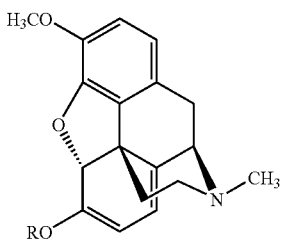

III is stirred with hydrogen peroxide or peroxoacids in the presence of oxalic acid and of another organic acid to form a crystalline precipitate of 14-hydroxycodeinone oxalate,
  wherein a base is added to said crystalline precipitate of 14-hydroxycodeinone oxalate to release 14-hydroxycodeinone of formula IV from said crystalline precipitate,

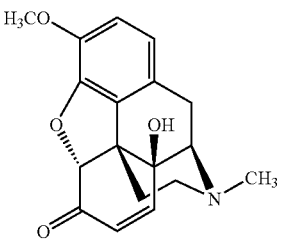

IV and wherein said 14-hydroxycodeinone of formula IV is hydrogenated with hydrogen in the presence of a catalyst to yield Oxycodone of formula I.

2. The method of preparation of Oxycodone according to claim 1, wherein the other organic acid is formic acid or acetic acid.

3. The method of preparation of Oxycodone according to claim 1, wherein the other organic acid is 80 to 90% formic acid.

4. The method of preparation of Oxycodone according to claim 1, wherein the concentration of hydrogen peroxide is 25 to 33%.

5. The method of preparation of Oxycodone according to claim 1, wherein the peroxoacid is peracetic acid, perbenzoic acid or m-chloroperbenzoic acid.

6. The method of preparation of Oxycodone according to claim 1, wherein the molar ratio of thebaine or its analogue: oxalic acid:the other organic acid:hydrogen peroxide or peroxoacid is 0.8-2:1:2.0-3.0:2.0-3.0.

7. The method of preparation of Oxycodone according to claim 1, wherein the temperature during the reaction of thebaine or its analogues with hydrogen peroxide or peroxoacids is 0 to 35° C.

8. The method of preparation of Oxycodone according to claim 1, wherein the crystalline precipitate of 14-hydroxycodeinone oxalate is separated by filtration, centrifugation or decantation, the solids are dissolved in water, 14-hydroxycodeinone is released by addition of a base, or the reaction mixture containing 14-hydroxycodeinone oxalate is alkalized by addition of a base and precipitated 14-hydroxycodeinone is separated by filtration, decantation or centrifugation.

9. The method of preparation of Oxycodone according to claim 1, wherein the pH in alkalization of the reaction mixture containing 14-hydroxycodeinone oxalate is 9 to 10.

10. The method of preparation of Oxycodone according to claim 1, wherein 14-hydroxycodeinone dissolved in the aqueous solution of organic acid is hydrogenated with hydrogen in the presence of a catalyst.

11. The method of preparation of Oxycodone according to claim 1, wherein the Oxycodone of formula I is used for the preparation of Oxycodone hydrochloride.

12. The method of preparation of Oxycodone according to claim 1, wherein the other organic acid is 88% formic acid.

13. The method of preparation of Oxycodone according to claim 1, wherein the molar ratio of thebaine or its analogue: oxalic acid: the other organic acid: hydrogen peroxide or peroxacid is 1.5-2.0:1:2.3-2.7:2.3-2.7.

14. The method of preparation of Oxycodone according to claim 1, wherein the temperature during the reaction of thebaine or its analogues with hydrogen peroxide or peroxoacids is 15 to 25° C.

15. The method of preparation of Oxycodone according to claim 1, wherein the pH in alkalization of the reaction mixture containing 14-hydroxycodeinone oxalate is 9.2 to 9.6.

* * * * *